(12) United States Patent
Chuter

(10) Patent No.: US 6,926,743 B1
(45) Date of Patent: Aug. 9, 2005

(54) BIOLOGICAL STENT-GRAFT

(76) Inventor: Timothy A. M. Chuter, University of California, San Francisco 505 Parnassus - M-488, San Francisco, CA (US) 94143

( * ) Notice: Subject to any disclaimer, the term of this patent is extended or adjusted under 35 U.S.C. 154(b) by 233 days.

(21) Appl. No.: 10/441,956

(22) Filed: May 20, 2003

Related U.S. Application Data

(60) Provisional application No. 60/382,097, filed on May 21, 2002.

(51) Int. Cl.$^7$ ................................................ A61F 2/06

(52) U.S. Cl. ...................................... 623/141; 623/145

(58) Field of Search ............................. 623/1.13, 1.27, 623/1.28, 1.29, 1.38–1.48

(56) References Cited

U.S. PATENT DOCUMENTS

| | | | |
|---|---|---|---|
| 4,388,735 A | 6/1983 | Ionescu et al. | |
| 5,376,110 A | 12/1994 | Tu et al. | |
| 5,961,549 A | 10/1999 | Nguyen et al. | |
| 6,060,640 A * | 5/2000 | Pauley et al. | 623/23.72 |
| 6,210,436 B1 * | 4/2001 | Weadock | 623/1.39 |
| 6,709,467 B1 * | 3/2004 | Kantsevitcha et al. | 623/1.41 |

* cited by examiner

*Primary Examiner*—Corrine McDermott
*Assistant Examiner*—Hieu Phan
(74) *Attorney, Agent, or Firm*—William G. Lane

(57) ABSTRACT

A biological stent-graft and a method of making the same wherein a stent is surgically implanted in the lumen of an artery of a mammal, harvesting the stent-graft precursor after the stent has been incorporated into artery wall, fixing the harvested stent-graft precursor, and washing the same to yield a biological stent-graft.

40 Claims, No Drawings

BIOLOGICAL STENT-GRAFT

This application claims the benefit of U.S. Provisional Application No. 60/382,097, filed on May 21, 2002.

BACKGROUND TO THE INVENTION

As the name implies, a stent-graft is the combination of a flexible, compressible conduit, or graft, and a structural framework, or stent. The graft is a continuous sealed walled conduit surrounding a central plenum opened at opposing ends for the transport of blood or other body fluids. The graft is used to bridge diseased or weakened portions of vessels, or other corporeal lumen.

Problems with the Current Supported Grafts

The structural functions of a stent and graft are difficult to incorporate into a single integral unit, because each has a different function and each requires different material properties. Hence, the use of two distinct components. The connection of one component to another has been problematic. In most applications, the stent-graft is introduced in a collapsed state into the vessel. After the stent-graft is positioned in the vessel it is then expanded within the target lumen area of the vessel. The change in diameter may cause separation of the one from the other. The current art has many examples of ways to bind the stent to the graft, including sewing the stent and graft together, sandwiching the stent between an inner and outer grafts, or sandwiching the graft between inner and outer stents. But none achieve full integration. The resulting problems from the lack of full integration include micro-movement, poor contact with surrounding lumen, and restriction of the lumen, and the like.

Micromovement between the stent and graft can lead to graft erosion. Lack of contact between the stent and graft can lead to perigraft leakage, i.e. leakage of body fluids around the outer wall of the graft, especially when the stent is on the outside of the graft. Conversely, when the stent is on the inside of the graft, i.e. in the graft lumen, it can snag catheters and guidewires during re-instrumentation. The size of the stent-graft profile and the delivery system for the stent-graft can increase with the additional layers of stent or graft used in the sandwich method of attachment. In addition redundant folds of graft which is a problem with dual layer sandwich graft-stents, can fold into the lumen, occluding or impeding blood flow or other bodily fluid flow.

The Biology of Stent Ingrowth

Once implanted in a vascular lumen, most stents become rapidly incorporated into the wall of the surrounding vessel by smooth muscle invasion, followed by collagen deposition and intimal migration. The process of ingrowth varies according to the type of stent and the type of artery. Balloon-expanded stents incorporate more rapidly than self-expanding stents, and healthy canine arteries infiltrate the stent structure more rapidly than aging human arteries. It is believed that age is or would be a factor in the ingrowth of a stent in any mammal. The ingrowth of skeletal structures or frames for grafts in other biological vessels, such as the urethra or esophagus, is not well under stood as this point.

DESCRIPTION OF THE INVENTION

The invention is a biologic stent-graft, in which the graft is derived from an animal blood vessel and the attachment between the stent and graft is a product of the natural process by which stents become incorporated into blood vessel walls through ingrowth. Thus the biological stent graft of the present invention comprises the integration of a non-biological stent made from a biologically acceptable material, such as medicinally accepted metals and/or polymers, with the tissue of a vessel (the graft) by the natural ingrowth occurring when the stent is implanted in a vessel, such as an arterial vessel, of an animal for a period of time sufficient to permit ingrowth.

The steps in biological stent-graft manufacture are as follows:

1. A metal or polymeric stent is surgically implanted in the lumen of a vessel, such as the artery, of a living animal.
2. The stent is left in place for a sufficient time for the arterial wall to incorporate the stent through tissue ingrowth to yield a stented vessel.
3. The stented vessel is surgically harvested to yield a biological stent-graft precursor.
4. The biological stent-graft precursor, i.e. harvested stented vessel, is washed and cleaned.
5. The washed and cleaned biological stent-graft precursor is fixed by one of the known methods used to fix pig valves, animal arterial vessels, animal arterial patches, and the like, to yield the biological stent-graft of the present invention. The fixation insures sterilization of the of the biological stent-graft, and makes the tissue inert to tissue rejection processes within a body.

Implantation

Canine, bovine and porcine arterial vessels at the present appear to be the most attractive source of vessels for biological stent-grafts. However other vessels, such as veins, and vessels from other animals, such as rabbit, may be equally suitable. The selection of vessel and the animal for implantation of the stent may depend on the size requirements as well as ingrowth rates. Cattle and pigs (including swine) might be the most convenient source because of the anatomical similarity of cattle and pig vessels and human vessels, and because cattle and pigs are raised for slaughter. The stents can be surgically implanted, i.e. intravascularly inserted, into the arterial vessels of young calves and pigs four to six moths prior to their scheduled slaughter. At slaughter the formed stented graft, i.e. biological stent-graft precursors, can be harvested from the steer and pigs under appropriate conditions to ensure cleanliness of the harvested stented vessel.

The type of stent, metal, plastic, expandable, and the like, the animal species, the implantation site in the animal, the type of vessel, and the fixation method can all be varied to alter the properties of the resulting biological stent-graft. Preferably the external diameter of the stent is only slightly less than the internal diameter of the vessel wall. The stent can be expanded partially when implanted to contact the vessel wall to secure the stent in the vessel and to speed up tissue incorporation of the stent into the vessel. The stents are made of biologically acceptable materials that are suitable for implantation, such as medicinally acceptable metals and/or polymers. For example, a small diameter, low profile biological stent-graft can be made by implanting a coronary stent in the thoracic aorta of a rabbit, allowing the ingrowth of smooth muscle and collagen into the stent to completely encapsulate the stent into the vessel wall to create a stented vessel, harvesting the stented vessel, washing and cleaning the harvested stented vessel, and fixing the washed and cleaned harvested stented vessel or biological stent-graft precursor to form the biological stent-graft. Preferably the surgical implantation is done endoscopically and/or endovascularly.

Harvesting

The stented vessel is removed from the sacrificed animal and immersed in a sterile saline solution, preferably cold. The harvested stented vessel, i.e. biological stent-graft precursor, is preferably washed and cleaned at a chilled temperature to minimize biological degradation. The biological stent-graft precursor is cut to length and excess connective tissue adhering to the biological stent-graft precursor is cut away. Unwanted branches, such as arterial branches, extending from the biological stent-graft precursor are ligated in accordance with standard medical practice. The biological stent-graft precursor can be given a final washing with sterile saline solutions and if stored, it is preferably stored in sterile saline solution, preferably at a cold temperature such as just above freezing.

Fixation of Biological Prostheses

Fixation is a general name for the process by which the proteins of a biologic tissue are denatured. The most important effects of fixation include: cross-linking of collagen; strengthening the collagen and rendering it resistant to enzymatic degradation; alteration of the surface proteins on collagen and tissue; rendering the collagen and tissue non-immunogenic; destroying cellular DNA and enzymes, and eliminating infectivity of tissue. Animal tissues, that have been treated by fixation, are widely used as prosthetic valves, arterial conduits, and arterial patches. There are numerous well known methods for fixing and denaturing proteinaceous tissue. For example glutaraldehyde solutions (0.25 to 1.0% solutions at a pH of around 7.4, and glycerol triglycidyl ether solutions (1.0 to 2.5% solutions at a pH of around 10.0) are suitable. Further information can be found in U.S. Pat. Nos. 4,388,735; 5,375,110; and 5,961,549; and the patents and references cited therein; the total disclosures of which are incorporated by reference herein. Glutaraldehyde fixation is relatively fast but renders the fixed tissue rather tough and less pliable, whereas glycerol triglycidyl ether fixation is relatively slow but renders the fixed tissue less tough and more pliable.

After fixation, the biological stent-graft is thoroughly washed with a sterile solution to remove substantially all, or all, the fixation agent and stored in sterile solution, such as ethanol. The biological stent-graft can be stored in a moist state. The biological stent-graft can optionally be stored at low temperatures such as near, but above, freezing.

The biological stent graft is employed in a patient in the same manner as existing non-biological surgical stent-grafts.

What is claimed is:

1. A method of making a biological stent-graft comprising the following steps:
   a stent is surgically implanted in the lumen of a blood vessel of a living animal; the stent is left in place for a sufficient time for the vessel wall to incorporate the stent through tissue ingrowth to yield a stented vessel;
   the stented vessel is surgically harvested to yield a biological stent-graft precursor;
   the biological stent-graft precursor is washed and cleaned; and
   the washed and cleaned biological stent-graft precursor is fixed with a fixation agent; and
   after fixation, the fixed biological stent-graft is washed with a sterile solution to remove substantially all of the fixation agent to yield the biological stent-graft.

2. The method according to claim 1 wherein the stent is surgically implanted in the lumen of an artery.

3. The method according to claim 1 wherein the stent is surgically implanted in the lumen of an artery of a mammal.

4. The method according to claim 1 wherein the stent is a metal stent.

5. The method according to claim 1 wherein the stent is a polymeric stent.

6. The method according to claim 1 wherein the living animal is a bovine.

7. The method according to claim 1 wherein the animal is a canine.

8. The method according to claim 1 wherein the animal is a porcine.

9. The method according to claim 1 wherein the stent is surgically implanted by endoscopic means.

10. The method according to claim 1 wherein the stent-graft is surgically implanted by endovascular means.

11. The method according to claim 1 wherein the stent is surgically implanted into the arterial vessels of a young calf or a young pig four to six months prior to the animal's scheduled slaughter.

12. The method according to claim 11 wherein the formed biological stent-graft precursor is harvested from the slaughtered calf or pig.

13. The method according to claim 1 wherein the stent is made of a biologically acceptable material that is suitable for implantation and ingrowth by the vessel wall.

14. The method according to claim 1 wherein the stent is partially expanded when implanted into the vessel wall to secure the stent in the vessel and to enhance tissue incorporation of the stent by the vessel wall.

15. The method according to claim 1 wherein unwanted branches extending from the biological stent-graft precursor are ligated after harvesting of the biological stent-graft precursor.

16. The method according to claim 1 wherein after harvesting, and fixing, the biological stent-graft precursor is washed with sterile solution and stored in a sterile solution.

17. The method according to claim 1 wherein the harvested biological stent-graft precursor is fixed with a solution of glutaraldehyde.

18. The method according to claim 17 wherein after fixation, the biological stent-graft is thoroughly washed with a sterile solution to remove all fixation agent.

19. The method according to claim 1 wherein the harvested biological stent-graft precursor is fixed with a solution of gycerol triglycidyl ether solutions.

20. The method according to claim 19 wherein after fixation, the biological stent-graft is thoroughly washed with a sterile solution to remove all fixation agent.

21. A biological stent-graft made by the process of:
   surgically implanting a stent in the lumen of a blood vessel of a living animal;
   the stent is left in place for a sufficient time for the vessel wall to incorporate the stent through tissue ingrowth to yield a stented vessel;
   the stented vessel is surgically harvested to yield a biological stent-graft precursor;
   the biological stent-graft precursor is washed and cleaned; and
   the washed and cleaned biological stent-graft precursor is fixed with a fixation agent; and
   after fixation, the biological stent-graft is washed with a sterile solution to remove substantially all of the fixation agent to yield the biological stent-graft.

22. The biological stent-graft according to claim 21 wherein the stent is surgically implanted in the lumen of an artery.

23. The biological stent-graft according to claim 21 wherein the stent is surgically implanted in the lumen of an artery of a mammal.

24. The biological stent-graft according to claim 21 wherein the stent is a metal stent.

25. The biological stent-graft according to claim 21 wherein the IS stent is a polymeric stent.

26. The biological stent-graft according to claim 21 wherein the living animal is a bovine.

27. The biological stent-graft according to claim 21 wherein the animal is a canine.

28. The biological stent-graft according to claim 21 wherein the animal is a porcine.

29. The biological stent-graft according to claim 21 wherein the stent is surgically implanted by endoscopic means.

30. The biological stent-graft according to claim 21 wherein the stent-graft is surgically implanted by endovascular means.

31. The biological stent-graft according to claim 21 wherein the stent is surgically implanted into the arterial vessels of a young calf or a young pig four to six months prior to the animal's scheduled slaughter.

32. The biological stent-graft according to claim 31 wherein the formed biological stent-graft precursor is harvested from the slaughtered calf or pig.

33. The biological stent-graft according to claim 21 wherein the stent is made of a biologically acceptable material that is suitable for implantation and ingrowth by the vessel wall.

34. The biological stent-graft according to claim 21 wherein the stent is partially expanded when implanted into the vessel wall to secure the stent in the vessel and to enhance tissue incorporation of the stent by the vessel wall.

35. The biological stent-graft according to claim 21 wherein unwanted branches extending from the biological stent-graft precursor are ligated after harvesting of the biological stent-graft precursor.

36. The biological stent-graft according to claim 21 wherein after harvesting, and fixing, the biological stent-graft precursor is washed with sterile solution and stored in a sterile solution.

37. The biological stent-graft according to claim 21 wherein the harvested biological stent-graft precursor is fixed with a solution of glutaraldehyde.

38. The biological stent-graft according to claim 37 wherein after fixation, the biological stent-graft is thoroughly washed with a sterile solution to remove all fixation agent.

39. The biological stent-graft according to claim 21 wherein the harvested biological stent-graft precursor is fixed with a solution of gycerol triglycidyl ether solutions.

40. The biological stent-graft according to claim 39 wherein after fixation, the biological stent-graft is thoroughly washed with a sterile solution to remove all fixation agent.

* * * * *